US011459415B2

(12) United States Patent
Youngblood et al.

(10) Patent No.: US 11,459,415 B2
(45) Date of Patent: *Oct. 4, 2022

(54) METHOD OF USING HYDROPHILIZED BACTERICIDAL POLYMERS

(71) Applicant: Purdue Research Foundation, West Lafayette, IN (US)

(72) Inventors: Jeffrey P. Youngblood, Crawfordsville, IN (US); Philippe H. Sellenet, Nancy (FR)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/115,709

(22) Filed: Dec. 8, 2020

(65) Prior Publication Data

US 2021/0084898 A1    Mar. 25, 2021

Related U.S. Application Data

(60) Continuation of application No. 15/163,285, filed on May 24, 2016, now Pat. No. 11,134,684, which is a division of application No. 14/837,900, filed on Aug. 27, 2015, now abandoned, which is a continuation of application No. 11/509,915, filed on Aug. 24, 2006, now abandoned.

(60) Provisional application No. 60/711,234, filed on Aug. 24, 2005.

(51) Int. Cl.
*A01N 43/40* (2006.01)
*C08F 220/28* (2006.01)
*C12Q 1/18* (2006.01)
*C08F 226/06* (2006.01)
*C08F 226/08* (2006.01)

(52) U.S. Cl.
CPC .......... *C08F 220/286* (2020.02); *A01N 43/40* (2013.01); *C08F 226/06* (2013.01); *C12Q 1/18* (2013.01); *C08F 220/281* (2020.02); *C08F 226/08* (2013.01)

(58) Field of Classification Search
CPC combination set(s) only.
See application file for complete search history.

(56) References Cited

U.S. PATENT DOCUMENTS

| | | |
|---|---|---|
| 2,717,887 A | 9/1955 | Saner |
| 2,882,157 A | 4/1959 | Thompson et al. |
| 2,972,535 A | 2/1961 | Laakso et al. |
| 3,140,227 A | 7/1964 | Roth et al. |
| 3,227,672 A | 1/1966 | Fertig et al. |
| 3,262,807 A | 7/1966 | Sterman et al. |
| 3,296,167 A | 1/1967 | Turner et al. |
| 3,296,196 A | 1/1967 | Lamoreaux |
| 3,328,328 A | 6/1967 | Scanley |
| 3,450,794 A | 6/1969 | Ebneth et al. |
| 3,592,805 A | 7/1971 | Szabo et al. |
| 3,597,313 A | 8/1971 | Coscia et al. |
| 3,619,200 A | 11/1971 | Ferguson et al. |
| 3,753,716 A | 8/1973 | Ishihara et al. |
| 3,871,376 A | 3/1975 | Kozak |
| 3,872,128 A | 3/1975 | Byck |
| 3,898,188 A | 8/1975 | Rembaum et al. |
| 3,929,741 A | 12/1975 | Laskey |
| 3,975,350 A | 8/1976 | Hudgin et al. |
| 4,011,178 A | 3/1977 | Muse |
| 4,017,440 A | 4/1977 | Killam |
| 4,026,941 A | 5/1977 | Login et al. |
| 4,029,694 A | 6/1977 | Weipert et al. |
| 4,069,365 A | 1/1978 | Rembaum |
| 4,070,189 A | 1/1978 | Kelley et al. |
| 4,080,315 A | 3/1978 | Login |
| 4,081,419 A | 3/1978 | Shimizu et al. |
| 4,093,676 A | 6/1978 | Weipert et al. |
| 4,098,842 A | 7/1978 | Login |
| 4,104,443 A | 8/1978 | Latta et al. |
| 4,119,094 A | 10/1978 | Micklus et al. |
| 4,125,110 A | 11/1978 | Hymes |
| 4,147,550 A | 4/1979 | Campbell et al. |
| 4,152,307 A | 5/1979 | Shibahara et al. |

(Continued)

FOREIGN PATENT DOCUMENTS

| | | |
|---|---|---|
| DE | 3339662 A1 | 5/1984 |
| DE | 19833062 A1 | 2/2000 |

(Continued)

OTHER PUBLICATIONS http://beta.merriam-webster.com/dictionary/derivative (Year: 2015).*
U.S. Appl. No. 11/509,915 Office Action dated Mar. 9, 2010.
U.S. Appl. No. 11/509,915 Amendment dated Aug. 9, 2010.
U.S. Appl. No. 11/509,915 Office Action dated May 12, 2011.
U.S. Appl. No. 11/509,915 Amendment dated Sep. 12, 2011.
U.S. Appl. No. 11/509,915 Advisory Action dated Sep. 29, 2011.
U.S. Appl. No. 11/509,915 Request for Continued Examination dated Oct. 11, 2011.
U.S. Appl. No. 12/549,004 Office Action dated May 4, 2012.
U.S. Appl. No. 12/549,004 Interview Summary dated Aug. 23, 2012.

(Continued)

*Primary Examiner* — James W Rogers
(74) *Attorney, Agent, or Firm* — Strategic Innovation IP Law Offices, P.C.; Charles D. Holland

(57) ABSTRACT

A bactericidal polymeric composition includes a hydrophilic first comonomer copolymerized to a second comonomer to produce a polymeric composition that is more hydrophilic or more bactericidal in an aqueous solution than either of the comonomers alone. Methods for identifying bactericidal polymers, methods for rendering materials bactericidal, and methods for using bactericidal compositions to kill or reduce bacterial growth are also described. Applications for the inventive compositions include their use in catheters, stents, medical devices, contact lenses; root canal fillers; and/or wound dressings.

13 Claims, 5 Drawing Sheets

(56) References Cited

U.S. PATENT DOCUMENTS

| | | |
|---|---|---|
| 4,181,752 A | 1/1980 | Martens et al. |
| 4,191,743 A | 3/1980 | Klemm et al. |
| 4,226,232 A | 10/1980 | Spence |
| 4,226,748 A | 10/1980 | Matsunaga et al. |
| 4,229,554 A | 10/1980 | Newkirk et al. |
| 4,234,381 A | 11/1980 | Killam |
| 4,256,800 A | 3/1981 | Stockhausen et al. |
| 4,259,411 A | 3/1981 | Windhager et al. |
| 4,304,703 A | 12/1981 | Das |
| 4,306,996 A | 12/1981 | Windhager |
| 4,318,947 A | 3/1982 | Joung |
| 4,332,919 A | 6/1982 | Kobayashi et al. |
| 4,361,623 A | 11/1982 | Newkirk et al. |
| 4,366,238 A | 12/1982 | Yokoyama et al. |
| 4,373,009 A | 2/1983 | Winn |
| 4,377,667 A | 3/1983 | Sakurai et al. |
| 4,384,078 A | 5/1983 | Ohya et al. |
| 4,391,278 A | 7/1983 | Cahalan et al. |
| 4,393,048 A | 7/1983 | Mason, Jr. et al. |
| 4,414,353 A | 11/1983 | Maslanka et al. |
| 4,416,668 A | 11/1983 | Thompson |
| RE31,454 E | 12/1983 | Hymes |
| 4,459,289 A | 7/1984 | Maltz |
| 4,480,075 A | 10/1984 | Willis |
| 4,482,680 A | 11/1984 | Sheldon et al. |
| 4,500,517 A | 2/1985 | Luss |
| 4,506,070 A | 3/1985 | Ben |
| 4,515,162 A | 5/1985 | Yamamoto et al. |
| 4,515,593 A | 5/1985 | Norton |
| 4,539,996 A | 9/1985 | Engel |
| 4,543,390 A | 9/1985 | Tanaka et al. |
| 4,546,140 A | 10/1985 | Shih |
| 4,563,184 A | 1/1986 | Korol |
| 4,570,629 A | 2/1986 | Widra |
| 4,581,821 A | 4/1986 | Cahalan et al. |
| 4,617,343 A | 10/1986 | Walker et al. |
| 4,632,881 A | 12/1986 | Trotz et al. |
| 4,657,006 A | 4/1987 | Rawlings et al. |
| 4,659,785 A | 4/1987 | Nagano et al. |
| 4,668,748 A | 5/1987 | Hardam et al. |
| 4,674,512 A | 6/1987 | Rolf |
| 4,699,146 A | 10/1987 | Sieverding |
| 4,705,709 A | 11/1987 | Vailancourt |
| 4,722,965 A | 2/1988 | Wong et al. |
| 4,728,323 A | 3/1988 | Matson |
| 4,735,991 A | 4/1988 | Guioth et al. |
| 4,740,546 A | 4/1988 | Masuda et al. |
| 4,762,862 A | 8/1988 | Yada et al. |
| 4,768,523 A | 9/1988 | Cahalan et al. |
| 4,769,013 A | 9/1988 | Lorenz et al. |
| 4,777,954 A | 10/1988 | Keusch et al. |
| 4,791,063 A | 12/1988 | Hou et al. |
| 4,810,567 A | 3/1989 | Calcaterra et al. |
| 4,816,508 A | 3/1989 | Chen |
| 4,831,098 A | 5/1989 | Watanabe et al. |
| 4,841,021 A | 6/1989 | Katritzky et al. |
| 4,842,768 A | 6/1989 | Nakao et al. |
| 4,848,353 A | 7/1989 | Engel |
| 4,857,585 A | 8/1989 | Leising |
| 4,857,590 A | 8/1989 | Gaggar et al. |
| 4,859,727 A | 8/1989 | Sasaki et al. |
| 4,876,278 A | 10/1989 | Taylor et al. |
| 4,877,687 A | 10/1989 | Azegami et al. |
| 4,891,306 A | 1/1990 | Yokoyama et al. |
| 4,898,908 A | 2/1990 | Lahalih et al. |
| 4,900,543 A | 2/1990 | Ritter et al. |
| 4,900,544 A | 2/1990 | Ritter et al. |
| 4,920,166 A | 4/1990 | Buysch et al. |
| 4,931,506 A | 6/1990 | Yu |
| 4,931,522 A | 6/1990 | Catena |
| 4,943,612 A | 7/1990 | Morita et al. |
| 4,947,847 A | 8/1990 | Nakao et al. |
| 4,948,720 A | 8/1990 | Chen et al. |
| 4,954,636 A | 9/1990 | Merianos et al. |
| 4,957,908 A | 9/1990 | Nelson |
| 4,981,936 A | 1/1991 | Good et al. |
| 4,997,697 A | 3/1991 | Malhotra |
| 4,999,249 A | 3/1991 | Deschler et al. |
| 5,004,760 A | 4/1991 | Patton et al. |
| 5,006,267 A | 4/1991 | Vaughn et al. |
| 5,010,139 A | 4/1991 | Yu |
| 5,019,096 A | 5/1991 | Fox, Jr. et al. |
| 5,024,840 A | 6/1991 | Blakely et al. |
| 5,043,195 A | 8/1991 | Skrivseth |
| 5,049,383 A | 9/1991 | Huth et al. |
| 5,055,171 A | 10/1991 | Peck |
| 5,057,560 A | 10/1991 | Mueller |
| 5,059,629 A | 10/1991 | Patton et al. |
| 5,061,752 A | 10/1991 | Buysch et al. |
| 5,069,907 A | 12/1991 | Mixon et al. |
| 5,080,097 A | 1/1992 | Eisenberg |
| 5,081,182 A | 1/1992 | Robinson et al. |
| 5,082,697 A | 1/1992 | Patton et al. |
| 5,124,076 A | 6/1992 | Smuckler |
| 5,142,010 A | 8/1992 | Olstein |
| 5,153,321 A | 10/1992 | Finter et al. |
| 5,175,059 A | 12/1992 | Yamamoto et al. |
| 5,183,576 A | 2/1993 | Wood et al. |
| 5,194,539 A | 3/1993 | Charmot et al. |
| 5,205,297 A | 4/1993 | Montecalvo et al. |
| 5,247,008 A | 9/1993 | Michels et al. |
| 5,255,979 A | 10/1993 | Ferrari |
| 5,263,481 A | 11/1993 | Axelgaard |
| 5,264,249 A | 11/1993 | Perrault et al. |
| 5,269,770 A | 12/1993 | Conway et al. |
| 5,271,943 A | 12/1993 | Bogart et al. |
| 5,290,894 A | 3/1994 | Melrose et al. |
| 5,312,863 A | 5/1994 | Van Rheenen et al. |
| 5,314,924 A | 5/1994 | Lee |
| 5,317,063 A | 5/1994 | Komatsu et al. |
| 5,330,527 A | 7/1994 | Montecalvo et al. |
| 5,336,717 A | 8/1994 | Rolando et al. |
| 5,346,956 A | 9/1994 | Gnanou |
| 5,354,790 A | 10/1994 | Keusch et al. |
| 5,358,688 A | 10/1994 | Robertson |
| 5,369,179 A | 11/1994 | Havens |
| 5,370,981 A | 12/1994 | Krafft et al. |
| 5,402,884 A | 4/1995 | Gilman et al. |
| 5,403,587 A | 4/1995 | McCue et al. |
| 5,403,640 A | 4/1995 | Krishnan et al. |
| 5,403,883 A | 4/1995 | Messner et al. |
| 5,420,197 A | 5/1995 | Lorenz et al. |
| 5,421,982 A | 6/1995 | Ikeda et al. |
| 5,429,590 A | 7/1995 | Saito et al. |
| 5,432,000 A | 7/1995 | Young, Sr. et al. |
| 5,447,643 A | 9/1995 | Kelkenberg et al. |
| 5,466,256 A | 11/1995 | McAdams et al. |
| 5,470,916 A | 11/1995 | Righetti et al. |
| 5,474,065 A | 12/1995 | Meathrel et al. |
| 5,480,717 A | 1/1996 | Kundel |
| 5,489,437 A | 2/1996 | Marra |
| 5,494,987 A | 2/1996 | Imazato et al. |
| 5,498,478 A | 3/1996 | Hansen et al. |
| 5,509,899 A | 4/1996 | Fan et al. |
| 5,512,329 A | 4/1996 | Guire et al. |
| 5,515,117 A | 5/1996 | Dziabo et al. |
| 5,518,788 A | 5/1996 | Invie |
| 5,520,180 A | 5/1996 | Uy et al. |
| 5,520,910 A | 5/1996 | Hashimoto et al. |
| 5,525,356 A | 6/1996 | Jevne et al. |
| 5,533,971 A | 7/1996 | Phipps |
| 5,536,446 A | 7/1996 | Uy et al. |
| 5,536,494 A | 7/1996 | Park |
| 5,536,861 A | 7/1996 | Robertson |
| 5,563,056 A | 10/1996 | Swan et al. |
| 5,591,799 A | 1/1997 | Bott et al. |
| 5,597,661 A | 1/1997 | Takeuchi et al. |
| 5,599,321 A | 2/1997 | Conway et al. |
| 5,608,021 A | 3/1997 | Uchiyama et al. |
| 5,614,538 A | 3/1997 | Nelson, Jr. |
| 5,614,586 A | 3/1997 | Tang et al. |
| 5,618,586 A | 4/1997 | Swarup et al. |
| 5,622,168 A | 4/1997 | Keusch et al. |
| 5,624,704 A | 4/1997 | Darouiche et al. |

(56) References Cited

U.S. PATENT DOCUMENTS

| | | |
|---|---|---|
| 5,645,968 A | 7/1997 | Sacripante et al. |
| 5,646,197 A | 7/1997 | Martin |
| 5,654,369 A | 8/1997 | Tsubaki et al. |
| 5,665,477 A | 9/1997 | Meathrel et al. |
| 5,667,913 A | 9/1997 | Chen et al. |
| 5,670,557 A | 9/1997 | Dietz et al. |
| 5,674,275 A | 10/1997 | Tang et al. |
| 5,674,561 A | 10/1997 | Dietz et al. |
| 5,688,855 A | 11/1997 | Stoy et al. |
| 5,700,742 A | 12/1997 | Payne |
| 5,725,789 A | 3/1998 | Huber et al. |
| 5,773,507 A | 6/1998 | Incorvia et al. |
| 5,779,632 A | 7/1998 | Dietz et al. |
| 5,798,048 A | 8/1998 | Ries |
| 5,798,096 A | 8/1998 | Pavlyk |
| 5,800,685 A | 9/1998 | Perrault |
| 5,821,280 A | 10/1998 | Suda et al. |
| 5,830,934 A | 11/1998 | Krishnan |
| 5,830,983 A | 11/1998 | Alex et al. |
| 5,834,561 A | 11/1998 | Fukumoto et al. |
| 5,849,045 A | 12/1998 | Chen et al. |
| 5,849,822 A | 12/1998 | Kido et al. |
| 5,874,184 A | 2/1999 | Takeuchi et al. |
| 5,886,098 A | 3/1999 | Ueda et al. |
| 5,907,017 A | 5/1999 | Ober et al. |
| 5,916,917 A | 6/1999 | Suh et al. |
| 5,967,714 A | 10/1999 | Ottersbach et al. |
| 5,984,102 A | 11/1999 | Tay |
| 5,985,990 A | 11/1999 | Kantner et al. |
| 5,997,815 A | 12/1999 | Anders et al. |
| 6,013,275 A | 1/2000 | Konagaya et al. |
| 6,015,836 A | 1/2000 | Martin |
| 6,022,553 A | 2/2000 | Anders et al. |
| 6,024,895 A | 2/2000 | Shimizu et al. |
| 6,038,464 A | 3/2000 | Axelgaard et al. |
| 6,039,940 A | 3/2000 | Perrault et al. |
| 6,045,919 A | 4/2000 | Alex et al. |
| 6,050,979 A | 4/2000 | Haemmerle et al. |
| 6,090,459 A | 7/2000 | Jadamus et al. |
| 6,096,800 A | 8/2000 | Ottersbach et al. |
| 6,103,368 A | 8/2000 | Fukuda et al. |
| 6,114,467 A | 9/2000 | Ober et al. |
| 6,127,105 A | 10/2000 | Vandenabeele |
| 6,187,856 B1 | 2/2001 | Incorvia et al. |
| 6,194,530 B1 | 2/2001 | Klesse et al. |
| 6,197,322 B1 | 3/2001 | Dutkiewicz et al. |
| 6,203,856 B1 | 3/2001 | Ottersbach et al. |
| 6,207,361 B1 | 3/2001 | Greener et al. |
| 6,218,492 B1 | 4/2001 | Hill et al. |
| 6,221,425 B1 | 4/2001 | Michal et al. |
| 6,242,526 B1 | 6/2001 | Siddiqui et al. |
| 6,248,811 B1 | 6/2001 | Ottersbach et al. |
| 6,251,967 B1 | 6/2001 | Perichaud et al. |
| 6,266,490 B1 | 7/2001 | Mukai et al. |
| 6,280,509 B1 | 8/2001 | Mallow |
| 6,319,883 B1 | 11/2001 | Graham et al. |
| 6,358,557 B1 | 3/2002 | Wang et al. |
| 6,368,587 B1 | 4/2002 | Anders et al. |
| 6,410,040 B1 | 6/2002 | Melrose et al. |
| 6,428,866 B1 | 8/2002 | Jadamus et al. |
| 6,482,781 B2 | 11/2002 | Graham et al. |
| 6,497,868 B1 | 12/2002 | Tanahashi |
| 6,500,981 B1 | 12/2002 | Weipert |
| 6,511,669 B1 | 1/2003 | Garnier et al. |
| 6,525,134 B1 | 2/2003 | Lacroix et al. |
| 6,537,663 B1 | 3/2003 | Chang et al. |
| 6,559,116 B1 | 5/2003 | Godfroid et al. |
| 6,583,228 B2 | 6/2003 | Nkansah et al. |
| 6,689,856 B2 | 2/2004 | L'alloret |
| 6,750,296 B2 | 6/2004 | Ober et al. |
| 6,767,647 B2 | 7/2004 | Swofford et al. |
| 6,797,743 B2 | 9/2004 | McDonald |
| 6,800,278 B1 | 10/2004 | Perrault et al. |
| 6,815,074 B2 | 11/2004 | Aguado et al. |
| 6,815,502 B1 | 11/2004 | Lang et al. |
| 6,821,943 B2 | 11/2004 | Avery et al. |
| 6,852,353 B2 | 2/2005 | Qiu et al. |
| 7,112,559 B1 | 9/2006 | Mayhall et al. |
| 8,343,473 B2 | 1/2013 | Youngblood et al. |
| 8,349,300 B2 | 1/2013 | Wells et al. |
| 9,131,683 B2 | 9/2015 | Gisser et al. |
| 9,289,378 B2 | 3/2016 | Karandikar et al. |
| 11,134,684 B2 | 10/2021 | Youngblood et al. |
| 2001/0007694 A1 | 7/2001 | Ottersbach et al. |
| 2001/0044482 A1 | 11/2001 | Hu et al. |
| 2001/0050478 A1 | 12/2001 | Schmitz |
| 2002/0037955 A1 | 3/2002 | Baumann et al. |
| 2002/0081923 A1 | 6/2002 | Artley et al. |
| 2002/0086160 A1 | 7/2002 | Qiu et al. |
| 2002/0139583 A1 | 10/2002 | Masui et al. |
| 2002/0168473 A1 | 11/2002 | Ottersbach et al. |
| 2002/0177828 A1 | 11/2002 | Batich et al. |
| 2003/0013624 A1 | 1/2003 | Graham et al. |
| 2003/0017194 A1 | 1/2003 | Joerger et al. |
| 2003/0019813 A1 | 1/2003 | Ottersbach et al. |
| 2003/0022576 A1 | 1/2003 | Ottersbach et al. |
| 2003/0049437 A1 | 3/2003 | Devaney et al. |
| 2003/0068440 A1 | 4/2003 | Ottersbach et al. |
| 2003/0091641 A1 | 5/2003 | Tiller et al. |
| 2003/0108507 A1 | 6/2003 | Clipson et al. |
| 2003/0161804 A1 | 8/2003 | Perron et al. |
| 2003/0229185 A1 | 12/2003 | Chen et al. |
| 2003/0236376 A1 | 12/2003 | Kindt-Larsen et al. |
| 2004/0009136 A1 | 1/2004 | Dubief et al. |
| 2004/0135967 A1 | 7/2004 | Carney et al. |
| 2004/0202639 A1 | 10/2004 | DeGrado et al. |
| 2005/0003163 A1 | 1/2005 | Krishnan |
| 2005/0008676 A1 | 1/2005 | Qiu et al. |
| 2005/0008839 A1 | 1/2005 | Cramer et al. |
| 2005/0013842 A1 | 1/2005 | Qiu et al. |
| 2005/0032931 A1 | 2/2005 | Naisby et al. |
| 2005/0053569 A1 | 3/2005 | Bavouzet et al. |
| 2005/0058844 A1 | 3/2005 | Rubner et al. |
| 2005/0065284 A1 | 3/2005 | Krishnan |
| 2005/0101740 A1 | 5/2005 | Mougin |
| 2006/0057209 A1 | 3/2006 | Chapman et al. |
| 2006/0083854 A1 | 4/2006 | Ober et al. |
| 2006/0189710 A1 | 8/2006 | Hayashi et al. |
| 2007/0048249 A1 | 3/2007 | Youngblood et al. |
| 2007/0053867 A1 | 3/2007 | Ober et al. |
| 2007/0106040 A1 | 5/2007 | Ober et al. |
| 2007/0149694 A1 | 6/2007 | Krishnan |
| 2008/0226584 A1 | 9/2008 | Krishnan |
| 2009/0081367 A1 | 3/2009 | Makuta et al. |
| 2009/0311302 A1 | 12/2009 | Youngblood et al. |
| 2012/0046378 A1 | 2/2012 | Sloan |
| 2013/0079481 A1 | 3/2013 | Youngblood et al. |
| 2013/0109794 A1 | 5/2013 | Polzin et al. |
| 2013/0115185 A1 | 5/2013 | Tamareselvy et al. |
| 2013/0136783 A1 | 5/2013 | Youngblood et al. |
| 2014/0080977 A1 | 3/2014 | Youngblood et al. |
| 2014/0127320 A1 | 5/2014 | Salamone et al. |
| 2015/0093424 A1 | 4/2015 | Lapitsky et al. |
| 2016/0053038 A1 | 2/2016 | Youngblood et al. |
| 2016/0262392 A1 | 9/2016 | Youngblood et al. |
| 2017/0360688 A1 | 12/2017 | Fevola et al. |
| 2018/0237686 A1 | 8/2018 | Schnoor et al. |
| 2018/0340046 A1 | 11/2018 | Hopkins et al. |
| 2018/0362678 A1 | 12/2018 | Hopkins et al. |
| 2020/0354527 A1 | 11/2020 | Hopkins et al. |
| 2020/0369800 A1 | 11/2020 | Hopkins et al. |

FOREIGN PATENT DOCUMENTS

| | | |
|---|---|---|
| DE | 19910811 | 9/2000 |
| EP | 0000426 A1 | 1/1979 |
| EP | 0085327 A1 | 8/1983 |
| EP | 0099209 | 1/1984 |
| EP | 0141628 A1 | 5/1985 |
| EP | 0239213 A2 | 9/1987 |
| EP | 0286009 A2 | 10/1988 |
| EP | 0337474 | 10/1989 |
| EP | 375350 A2 | 6/1990 |
| EP | 0204312 B1 | 8/1990 |

(56) References Cited

FOREIGN PATENT DOCUMENTS

| | | |
|---|---|---|
| EP | 0469196 A1 | 2/1992 |
| EP | 0604369 A1 | 6/1994 |
| EP | 0290676 B1 | 8/1994 |
| EP | 0747456 A2 | 12/1996 |
| EP | 1109845 B1 | 10/2005 |
| GB | 1299012 | 12/1972 |
| GB | 1350400 A | 4/1974 |
| GB | 2091277 A | 7/1982 |
| JP | H05286811 | 11/1993 |
| JP | 2002-105152 | 4/2002 |
| WO | WO 91/12282 | 8/1991 |
| WO | WO 92/06694 | 4/1992 |
| WO | WO 95/27530 | 10/1995 |
| WO | WO 97/14448 | 4/1997 |
| WO | WO 97/15603 | 5/1997 |
| WO | WO97/35542 | 10/1997 |
| WO | WO 97/45468 | 12/1997 |
| WO | WO 98/19311 | 5/1998 |
| WO | WO 98/29463 | 7/1998 |
| WO | WO 98/51720 | 11/1998 |
| WO | WO 99/09837 | 3/1999 |
| WO | WO 00/05283 | 2/2000 |
| WO | WO 00/08077 | 2/2000 |
| WO | WO 00/71591 A1 | 11/2000 |
| WO | WO03/028767 A2 | 4/2003 |
| WO | WO2004/045755 A2 | 6/2004 |
| WO | WO2013/185058 A2 | 12/2013 |
| WO | WO2016/127387 A1 | 8/2016 |
| WO | WO2017/003923 A1 | 1/2017 |
| WO | WO2018/222622 A1 | 12/2018 |
| WO | WO2018/232417 A1 | 12/2018 |

OTHER PUBLICATIONS

U.S. Appl. No. 12/549,004 Interview Summary dated Sep. 11, 2012.
U.S. Appl. No. 12/549,004 Amendment dated Sep. 13, 2012.
U.S. Appl. No. 12/549,004 Notice of Allowance dated Nov. 19, 2012.
U.S. Appl. No. 13/682,159 Office Action dated Mar. 1, 2013.
U.S. Appl. No. 11/509,915 Office Action dated Jun. 13, 2013.
U.S. Appl. No. 13/682,159 Amendment dated Jun. 28, 2013.
U.S. Appl. No. 13/682,159 Office Action dated Aug. 20, 2013.
U.S. Appl. No. 13/748,290 Office Action dated Aug. 22, 2013.
U.S. Appl. No. 11/509,915 Amendment dated Nov. 13, 2013.
U.S. Appl. No. 11/509,915 Office Action dated Jan. 7, 2014.
U.S. Appl. No. 14/087,188 Office Action dated Mar. 7, 2014.
U.S. Appl. No. 14/087,188 Response dated Sep. 8, 2014.
U.S. Appl. No. 14/087,188 Office Action dated Nov. 6, 2014.
U.S. Appl. No. 11/509,915 Amendment dated Dec. 8, 2014.
U.S. Appl. No. 11/509,915 Office Action dated Feb. 26, 2015.
U.S. Appl. No. 14/087,188 Pre-Appeal Conference Request dated May 6, 2015.
U.S. Appl. No. 14/837,900 Office Action dated Jan. 25, 2016.
U.S. Appl. No. 14/837,900 Amendment dated Apr. 21, 2016.
U.S. Appl. No. 14/837,900 Office Action dated Jun. 8, 2016.
U.S. Appl. No. 15/163,285 Office Action dated Nov. 21, 2016.
U.S. Appl. No. 14/837,900 Notice of Appeal dated Dec. 8, 2016.
U.S. Appl. No. 15/163,285 Amendment dated Mar. 21, 2017.
U.S. Appl. No. 15/163,285 Office Action dated May 9, 2017.
U.S. Appl. No. 15/163,285 Amendment dated Feb. 9, 2018.
U.S. Appl. No. 15/163,285 Office Action dated May 15, 2018.
U.S. Appl. No. 15/163,285 Amendment dated Aug. 15, 2018.
U.S. Appl. No. 15/163,285 Office Action dated Oct. 19, 2018.
U.S. Appl. No. 15/163,285 Notice of Appeal dated Jan. 22, 2019.
U.S. Appl. No. 15/163,285 Appeal Brief dated Jun. 20, 2019.
U.S. Appl. No. 15/163,285 Examiners Answer dated Aug. 14, 2019.
U.S. Appl. No. 15/163,285 Reply Brief dated Oct. 14, 2019.
U.S. Appl. No. 15/992,033 Office Action dated Jan. 24, 2020.
U.S. Appl. No. 16/011,579 Office Action dated Feb. 14, 2020.
U.S. Appl. No. 16/993,761 Preliminary amendment dated Nov. 11, 2020.
U.S. Appl. No. 15/163,285 RCE and amendment dated Dec. 10, 2020.
U.S. Appl. No. 16/938,680 Preliminary amendment dated Dec. 17, 2020.
PCT/US2018/034954 PCT International Search Report and Written Opinion dated Jul. 12, 2018.
PCT/US2018/038126 PCT International Search Report and Written Opinion dated Aug. 24, 2018.
PCT/US2018/034954 Chapter II Demand and Response to Written Opinion dated Mar. 26, 2019.
PCT/US2018/034954 Second Written Opinion dated Apr. 30, 2019.
PCT/US2018/034954 Chapter II International Preliminary Report on Patentability dated Sep. 3, 2019.
EP18731331.7 Response and amendment dated Jul. 24, 2020.
EP18740003.1 Response and amendment dated Oct. 28, 2020.
Abel, et al., "Preparation and Investigation of Antibacterial Carbohydrate-Based Surfaces", Carbohydrate Research, vol. 337, No. 24; pp. 2495-2499; Nov. 29, 2002.
Allison, et al., "Hemocompatibility of Hydrophilic Antimicrobial Copolymers of Alkylated 4-Vinylpyridine" Biomacromolecules; 2007, 8; pp. 2995-2999.
Borman, "Surfaces Designed to Kill Bacteria", Chemical & Engineering News; vol. 80, No. 22; pp. 36-38; Jun. 10, 2002.
Docherty, K., et al., "Toxicity and Antimicrobial Activity of Imidazolium and Pyridinium Ionic Liquids", Green Chemistry, vol. 7, pp. 185-189, Mar. 14, 2005, DOI: 10.1039/b419172b.
Kawabata, et al., "Antibacterial Activity of Soluble Pyridinium-Type Polymers", Applied and Environmental Microbiology; vol. 54, No. 10; pp. 2532-2535; Oct. 1988.
Krishnan, et al., "Antibacterial Coatings Based on Quaternized Poly(4-Vinylpyridine) Block Copolymers", Polymeric Materials: Science and Engineering; vol. 91; pp. 814-815; 2004.
Kugler, R., et al., "Evidence of a Charge-Density Threshold for Optimum Efficiency of Biocidal Cationic Surfaces", Microbiology, 151, 2005, pp. 1341-1348, DOI: 10.1099/mic.0.27526-0.
Li, et al., "Bactericidal Ability of a Soluble Pyridinium-Type Polymer Under Different Conditions"; pp. 177-178; National American Chemical Society Meeting, Anaheim, CA; Mar. 21-25, 1999.
Li, et al., "Effect of the Macromolecular Chain Structure of a Soluble Pyridinium-Type Polymer on Antimicrobial Activity"; pp. 175-176; National American Chemical Society Meeting, Anaheim, CA; Mar. 21-25, 1999.
Lin, et al., "Insights Into Bactericidal Action of Surface-Attached Poly(vinyl-N-hexylpyridinium) Chains", Biotechnology Letters, vol. 24, No. 10; pp. 801-805; May 2002.
Lin, et al., "Mechanism of Bactericidal and Fungicidal Activities of Textiles Covalently Modified With Alkylated Polyethylenimine", Biotech. Bioeng.; vol. 83, No. 2; pp. 168-172; Jul. 20, 2003.
Napper, D.H., "Steric Stabilization", Department of Physical Chemistry, University of Sydney, Journal of Colloid and Interface Science, vol. 58, No. 2, Feb. 1977, ISSN 0021-9797, pp. 390-407.
Sellenet, et al., "Hydrophilized Pyridinium Bactericidal Polymers", Fall National American Chemical Society Meeting, Washington, DC; Aug. 28-Sep. 1, 2005; pp. 2.
Sellenet, et al., "Synergistic Activity of Hydrophilic Modification in Antibiotic Polymers" Biomacromolecules; 2007, vol. 8, No. 1; pp. 19-23.
Sellenet, "Hydrophilized Bactericidal Polymers", Thesis, Purdue University, MSE, Dec. 2004; pp. 83.
Tadros, Tharwat F., "Emulsion Formation, Stability, and Rheology", pp. 1-75, 2013.
Tiller, et al., "Designing Surfaces That Kill Bacteria on Contact", Proc. Natl. Acad. Sci. USA; vol. 98, No. 11; pp. 5981-5985; May 22, 2001.
Tiller, et al., "Polymer Surfaces Derivatized With Poly(Vinyl-N-Hexylpyridinium) Kill Airborne and Waterborne Bacteria"; Biotechnology and Bioengineering;vol. 79, No. 4; pp. 465-471; Aug. 20, 2002.
Waschinski, C., et al., "poly(oxazoline)s with Telechelic Antimicrobial Functions", Biomacromolecules 2005, vol. 6, No. 1, pp. 235-243.

(56) References Cited

OTHER PUBLICATIONS

Wynne, et al., "Novel Polymer Bound Bactericidal Surfaces"; vol. 45, No. 2; pp. 521-522; Fall National American Chemical Society Meeting, Philadelphia, PA; Aug. 22-27, 2004.
Alternative Medicine Review, Undecylenic Acid Monograph, vol. 7, No. 1, 2002, pp. 68-70.
Selected Abstracts; Dec. 2004-Mar. 2005; pp. 3.
Surface Industry, Detergent Raw Material, Sodium Tripolyphosphate 94.0% (STPP Industrial Grade), pp. 1-2, XP055579364.
XP002783622, Database WPI, Week 199349, Thomson Scientific, London, GB, AN 1993-389137, pp. 4.
Oxford Dictionary of Chemistry, 6th Edition, 2008, pp. 134-135 and 203.
"Sodium Dodecylbenzene Sulfonate (SDBS)", USDA Technical Evaluation Report, May 26, 2017, pp. 1-21.
U.S. Appl. No. 15/163,285 Office Action dated Aug. 20, 2021.
U.S. Appl. No. 15/163,285 Notice of Allowance dated Aug. 30, 2021.
U.S. Appl. No. 16/938,680 Office Action dated Jan. 4, 2022.

\* cited by examiner

METHOD OF USING HYDROPHILIZED BACTERICIDAL POLYMERS

CROSS REFERENCE TO RELATED APPLICATIONS

This application is a continuation of U.S. application Ser. No. 15/163,285 filed May 24, 2016, which is a divisional of Ser. No. 14/837,900 filed Aug. 27, 2015, which is a continuation of U.S. application Ser. No. 11/509,915 filed Aug. 24, 2006, and this application also claims the benefit of priority under 35 U.S.C. Section 119(e) to U.S. Provisional Application No. 60/711,234, filed Aug. 24, 2005, each of which is hereby incorporated by reference in its entirety as if put forth in full below.

BACKGROUND

There is an ever-growing demand for materials suitable for killing harmful microorganisms. Such materials could be used to coat surfaces of common objects touched by people to render them antiseptic so as to prevent transmission of bacterial infections or to facilitate the killing of microorganisms in solution.

Various polycations are known to have bactericidal properties. However, their bactericidal properties can be strongly influenced by whether the polycation or a composition containing the polycation is soluble. In some instances, the bactericidal property is most apparent in an insoluble form, which is not particularly amenable to killing microorganisms. In other instances, the bactericidal activity is lost when the polycation is cross-linked or otherwise rendered insoluble. Application of bactericidal polymers may also be limited by their use in brushes, their insolubility in solution, or by their unfavorable biocompatibility characteristics. Accordingly, there is a need for bactericidal formulations possessing having improved bactericidal, hydrophilicity/wettability and biocompatibility characteristics suitable for rendering materials or areas bactericidal and for killing airborne and/or waterborne microorganisms.

BRIEF SUMMARY

The present invention is directed to polymeric compositions providing improved bactericidal, hydrophilicity/wettability, and biocompatibility characteristics. In particular, the present invention provides a bactericidal composition, including a hydrophilic first comonomer polymerized to a second comonomer to form a polymeric composition, where the polymeric composition is more soluble and/or more bactericidal in an aqueous solution than either of the first comonomer or the second comonomer alone.

In a particular example, the present invention provides a quaternized bactericidal composition, in which poly(4-vinylpyridine) (PVP) is copolymerized with hydroxyethylmethacrylate (HEMA) or poly(ethyleneglycol) methacrylate (PEGMA).

In another example, the present invention provides a method for rendering a material or area bactericidal in which a bactericidal composition of the present invention is applied to a medium or device in an amount suitable for killing or significantly reducing the number of bacteria in or on the treated medium or device compared to an untreated medium or device.

In another example, the present invention provides a method for killing or significantly reducing the number of bacteria on a material or area treated with a bactericidal composition of the present invention.

In a further example, the present invention provides a method for identifying a polymer having suitable bactericidal activity in which a hydrophilic first comonomer is polymerized to a second comonomer to form a bactericidal polymeric composition, where the polymeric composition is determined to have suitable bactericidal activity if the polymeric composition has a higher bactericidal activity in an aqueous solution than either of the hydrophilic first comonomer or second comonomer alone (or treated similarly as the polymeric composition).

Applications for the inventive compositions include their use in catheters, needles, sutures, stents and other implantable medical devices, contact lenses, root canal fillers, wound dressings, burn dressings, tissue culture plates, and the like.

DETAILED DESCRIPTION

Figure 1:
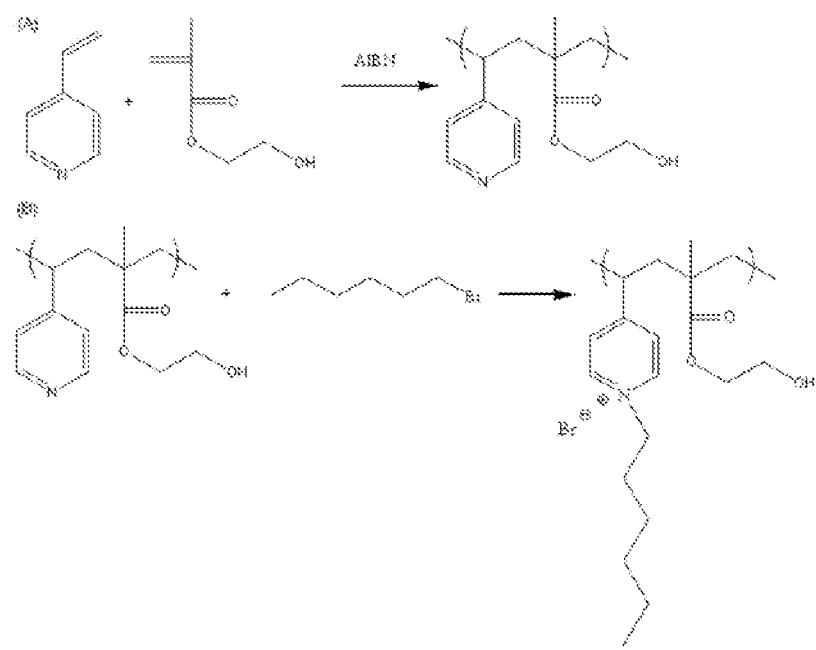
FIG. 1 is a schematic showing (A) the radical polymerization of P(VP-co-HEMA) and (B) quaternization of P(VP-co-HEMA)-HB.

In order to provide a clearer and consistent understanding of the specification and claims, the following definitions are provided. Unless defined otherwise, all technical and scientific terms have the same meaning as is commonly understood by one of skill in the art to which this invention belongs.

The term "monomer" refers to a relatively simple compound, usually containing carbon and of low molecular weight, which can react to form a polymer by combining with itself or with other monomers.

The terms "polymer" and "polymeric composition" are used interchangeably to denote a product of a polymerization reaction, and are inclusive of homopolymers, copolymers, terpolymers, etc.

The terms "polymerization" and "polymerization reaction" are inclusive of homopolymerizations, copolymerizations, terpolymerizations, and the like, and include all types of copolymerizations such as random, graft, block, and the like. In general, the polymers in the bactericidal composition on may be prepared in accordance with any suitable polymerization process, including slurry polymerization, solution polymerization, emulsion polymerization, gas phase polymerization, and high pressure polymerization and the like.

The term "comonomer" refers to a monomer, copolymer, or polymer which can copolymerize with itself or with at least one different monomer, copolymer, or polymer in a copolymerization reaction, the result of which can be a polymer, copolymer or polymeric composition.

The term "copolymer" refers to a polymer which can copolymerize with itself or with at least one different comonomer, polymer, or copolymer in a polymerization reaction or it can refer to a product resulting from a polymerization reaction of two comonomers. The copolymer may be identified or named in terms of the monomer(s) from which the copolymer is produced.

The terms "corresponding comonomer," "corresponding copolymer," and "corresponding polymer" are used to relate comonomers, copolymers, or polymers, respectively, sharing a common set of monomeric units between e.g. distinct polymeric compositions. The common comonomers, copolymers, or polymer need not be identical in terms of the molecular weight(s) or molar ratio(s) of commonly shared monomeric units.

The phrase "corresponding molecular weight" is used to relate molecular weight(s) of corresponding comonomers, copolymers, or polymers, respectively, in distinct polymeric compositions in which the common comonomers, copolymers, or polymers differ from one another by molecular weight(s) or commonly shared monomeric units within the corresponding comonomer, copolymer or polymer.

The phrase "corresponding molar ratio" is used to relate molar ratio(s) of corresponding comonomers, copolymers, or polymers, respectively, in distinct polymeric compositions in which the common comonomers, copolymers, or polymers differ from one another by molar ratio(s) or commonly shared monomeric units within the corresponding comonomer, copolymer or polymer.

The term "bactericidal" is used to interchangeably denote any one of the following: (i) a comonomer, polymer, copolymer, polymeric composition suitably formulated to kill, reduce the growth, number, viability and/or metabolic activity of one or more bacteria; (ii) a material, substance, medium, device, or area treated with a bactericidal comonomer, polymer, copolymer, polymeric composition so as to kill, reduce the growth, number, viability and/or metabolic activity of one or more bacteria.

The term "aqueous solution" refers to a solution in which water is the solvent.

The term "medium" refers to a treatable material, treatable substance, treatable device, or treatable area in which "treatable" refers to a capacity to be rendered bactericidal by a bactericidal comonomer, polymer, or copolymer. A treatable medium may have a defined physical form, but may include liquid (e.g., water, aqueous solution) or gaseous materials (e.g., air) also.

The phrases "significantly reducing the growth of bacteria" and "significantly reducing bacterial growth" are used interchangeably to denote one or more of the following conditions, including (i) a condition in which the metabolic activity of at least 50% of the microorganisms of a particular type exposed to a treated medium is terminated or reduced compared to bacteria of that particular type exposed to an untreated medium over a fixed period of time; (ii) a condition where there is 50% or less of one or more bacterial types present in and/or on a treated medium compared to the number of bacteria exposed to an untreated medium; and/or (iii) a condition resulting when one or more types of bacteria adhere 50% less to a treated medium compared to an untreated medium. The degree of bacterial growth reduction with respective to conditions (i)-(iii) may range from 50% to greater 99.9%.

The phrase "significantly bactericidal" denotes a comonomer, polymer, copolymer, composition, polymeric composition, material, substance or treated area in which the bactericidal comonomer, polymer, copolymer, composition, polymeric composition, material, substance or treated area is suitably formulated to significantly reduce the growth, number, viability and/or metabolic activity of bacteria by at least 50%.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

A bactericidal polymeric composition of the present invention includes a hydrophilic first comonomer polymerized to a second comonomer, where the polymeric composition is more soluble and/or more bactericidal in an aqueous solution than either of the first comonomer or the second comonomer alone. The polymeric composition of the present invention was found to have unexpected hydophilizing and/or wettabiliy properties providing enhanced bactericidal activity compared to either comonomer alone.

The second comonomer may be inherently bactericidal or it may be rendered bactericidal after a subsequent step (e.g., polymerization) and/or chemical modification (e.g., quaternization) of alkyl groups. Where the polymeric composition is further modified by chemical modification, such as quaternization, preferably, the polymeric composition is more hydrophilic and/or bactericidal than a similarly modified (by e.g., quaternization) second comonomer alone.

Bactericidal comonomers or those capable of being rendered bactericidal are copolymerized to a hydrophilizing comonomer. Exemplary second comonomers for polymerization to a hydrophilizing comonomer may include a variety of vinyl monomers capable of free radical polymerization and/or quaternization. Accordingly, these comonomers may include, but are not limited to, vinyl amines, such as N,N-dimethylvinylamine; allyl amines; vinyl esters, such as vinyl acetate; alkyl acrylates; and vinyl chloride. In a preferred embodiment, a pyridinium-type comonomer, such as vinyl pyridine or 4-vinylpyridine, is quaternized after polymerization to a hydrophilizing comonomer.

The second comonomer composition may include or be chemically linked to a suitable bactericidal moiety, including, but not limited to polycationic species, polycationic derivatives or combinations therefrom. Polycationic species may contain two or more quaternary ammonium groups with a molecular weight ranging from several hundred Daltons to a few hundred thousand Daltons. The quaternary ammonium groups may be part of a ring or they may be acyclic. Examples include but are not limited to: polyionenes, poly (diallyldimethylammonium chloride), dimethylamine-epichlorohydrin copolymers and imidazole-epichlorohydrin copolymers. Suitable bactericidal comonomers for use in the present invention may include the quaternary ammonium group-containing polymers disclosed in U.S. Pat. No. 4,482,680, which are incorporated by reference herein.

Polycationic species may contain two or more amine groups. The amine groups can be primary, secondary, tertiary, or mixtures thereof. The amine groups may be part of a ring or they may be acyclic. Examples include but are not limited to: polyethyleneimines, polypropyleneimines, polyvinylamines, polyallylamines, polydiallylamines, polyamidoamines, polyaminoalkylmethacrylates, polylysines, and mixtures thereof.

The polycationic species may also be a modified polyamine with at least one amine group substituted with at least one other functional group. Examples include ethoxylated and alkoxylated polyamines and alkylated polyamines. Other suitable bactericidal comonomers or those that may be rendered bactericidal may be identified and/or used in accordance with the applications and objectives set forth in the specification and claims.

Quaternization may be carried out using alkylating agents, including but not limited to alkyl halides (such as hexyl bromide), alkyl sulfonates, alkyl mesylates, alkyl tosylates, or other alkylating agents possessing a suitable leaving group. Quaternization reduces self-polymerization of the bactericidal comonomer upon polymerization with the hydrophilizing comonomer. Quaternization may confer increased bactericidal activity and is typically carried out after polymerization, since quaternized polymers are unpolymerizable.

Quaternized alkyl groups and/or other cationic chains may be attracted to and/or promote interaction and penetration negatively charged bacterial cell walls on account of their lipophilic nature. Alkyl chain lengths of quaternizing agents and overall hydrophilic/lipophilic balance may affect bactericidal activity of the polymeric compositions of the present invention. Accordingly, these variables may be modified to optimize or improve bactericidal activity of the polymeric compositions.

Hydrophilizing comonomers of the present invention confer increased wettability or hydrophilicity to one or more surfaces of the polymeric composition in aqueous solutions, including water. Preferably, the polymeric composition is more wettable than a bactericidal comonomer or a comonomer rendered bactericidal by quaternization, such as poly (4-vinylpyridine). Suitable hydrophilizing monomers or copolymers, may include, but are not limited to, ethylene glycol (ethylene oxide); polyethylene glycol derivatives, including poly(ethyleneglycol) methacrylate (PEGMA), poly(ethyleneglycol) acrylate, and vinyl polyethylene glycol; vinyl acetate; poly(vinyl alcohol); vinyl pyrrolidone and poly(vinyl pyrrolidone); vinyl pyrrolidinone and poly(vinyl pyrrolininone); vinyl oxazoline and poly(vinyl oxazoline); vinyl formamide and poly(vinyl formamide); hydroxyalkyl acrylates and hydroxyalkyl methacrylates, such as hydroxyethyl methacrylate (HEMA) and hydroxyethyl acrylate; methacrylamide; acrylamide and methacrylamide based monomers, such as acrylamide, N,N-dimethyl acrylamide, N-ethyl acrylamide, N-isopropyl acrylamide, and hydroxymethyl acrylamide; monomers containing one or more of the following functional groups: hydroxy, amino, ammonium, ether, carboxylate, amide, and sulfonamide groups; and combinations or copolymers thereof. polyvinyloxazolines Hydrophilic polymeric compositions and methods for hydrophilizing polymeric materials, including the use of high energy treatments, are disclosed in U.S. Pat. Appl. No. 20050008839, the contents of which are expressly incorporated by reference in their entirety, also may be used.

Preferably, the hydrophilizing comonomer is biocompatible. Standard assays may be utilized to evaluate biocompatibility, including but not limited to viability/cytotoxicity mammalian cell assays and the like. Representative hydrophilizing comonomers or copolymers include hydroxyethylmethacrylate (HEMA) and poly(ethyleneglycol) methacrylate (PEGMA).

HEMA is widely used in biomedical applications and devices, most prominently soft contact lenses. HEMA, with 37.8% water per weight, is typical of hydrogels. Preferably, the molar ratio of HEMA comonomer in the polymeric composition is equal to or greater than about 90 to 1.

PEGMA is a biocompatible polymer which possesses several important properties, such as good solubility in both organic and aqueous media, low toxicity, immunogenicity and nonbiodegradability.

Preferably, the molar molecular weight of PEGMA comonomer in the bactericidal composition is equal to or greater than 300, more preferably between about 300 and about 2000, including but not limited to 1100. Preferably, the molar ratio of PEGMA comonomer in the polymeric composition is equal to or less than about 10 to 1; equal to or less than about 25 to 1; equal to or greater than about 75 to 1; equal to or greater than about 95 to 1; equal to or greater than about 99 to 1.

Hydrophilicity or wettability can be evaluated by any suitable methodology known in the art, including contact angle testing and tensionometry testing. Contact angle testing of polymeric compositions may be carried out by dip coating microscope slides in solutions with copolymer dissolved in chloroform and methanol and obtaining contact angle measurements using e.g., a Ramé-Hart Advanced Goniometer. Contact angles may be characterized as advancing or receding, the difference being whether or not the angle is taken when moving onto a dry surface or moving off a wet surface. Advancing angles may be used for surface energy determinations, receding angles for characterizing other surface characteristics.

Polymeric bactericidal compositions may be rendered hydrophilic by engineering them to have advancing contact angles with water of less than or equal to about 90 degrees, preferably less than or equal to about 45 degrees, more preferably less than or equal to about 30 degrees, less than or equal to 15 degrees after 30 seconds of spreading.

The disclosed bactericidal compositions are suitably formulated to significantly reduce the growth, number, viability and/or metabolic activity of bacteria. A bactericidal composition may be formulated to significantly reduce bacterial growth from a treated medium by a factor of at least 50%. Further, a bactericidal composition may be formulated to significantly reduce bacterial growth from a treated medium by at least 60%, by at least 70%, by at least 80%, by at least 90%, by at least 95%, by at least 99%, or by at least 99.9%.

The bactericidal composition may be applied as a coating to at least one portion or surface of a medium or medical device, including but not limited to catheters, needles, stents, and other implantable medical devices. Various methods may be used to apply the comonomers or bactericidal polymers as a coating to the surface of the medical device. Suitable methods for applying coatings may include, but are not limited to the methods disclosed in U.S. Pat. Nos. 5,509,899 and 6,221,425, the contents of which are expressly incorporated by reference in their entirety.

Comonomers may be applied to a surface and subsequently polymerized. Alternatively, the bactericidal polymer composition may be applied directly to the surface of the medical device. In particular, one or more comonomers or bactericidal polymers may be combined with water and sprayed onto the medical device. Alternatively, the medical device may be dipped into a solution containing the bactericidal polymer. The comonomer or bactericidal polymer may be present in the solution in an amount from about 50% to about 98% by weight, particularly from about 70% to about 90% by weight, and applied to the surface of the medical device.

The viscosity of the monomeric or polymeric solution can be adjusted depending upon the particular application and circumstances. In general, when dipping the medical device into the solution, higher viscosities will cause more of the bactericidal polymer to remain on the surface of the device. Thus, if thicker coatings are desired, the viscosity can be increased. The viscosity of the solution can be increased by minimizing the amount of water in the solution. Additionally, thickeners, such as a polyacrylamide, can be added to the solution. The viscosity of the solution may also be increased by partially polymerizing the monomer.

In another example, the present invention provides methods for rendering a material or area bactericidal. In a further example, the present invention provides a method for killing or significantly reducing the number of bacteria on a material or area treated with a bactericidal composition of the present invention.

Accordingly, in one example, a bactericidal composition of the present invention is applied to a medium or medical device in an amount sufficient to kill or significantly reducing the number of bacteria in or on the treated medium compared to an untreated medium. In a further example, a bactericidal composition according to the present invention is applied to a medium or medical device in an amount sufficient to kill at least one bacterium or significantly reduce bacterial growth compared to an untreated medium.

The bacteria may be Gram-positive or Gram-negative. The bactericidal composition may be included in or coated onto a catheter, stent, implantable medical device, contact lens, root canal filler, or wound dressing. The treated medium may include natural or synthetic materials, implantable devices, or bodily surfaces. The treated medium may be contact with an aqueous environment, such as water or the inside of a patient or other vertebrate organism. Alternatively, the treated medium may be contact with air or air and/or air borne bacteria in an external environment or an enclosed bodily organ, such as lung.

Biocompatibility may be evaluated by any suitable methodology known in the art, including biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." In addition, any of the viability/cytotoxicity assays known to those of ordinary skill in the art may be used to evaluate lack of toxicity for normal human cells.

In a further example, the present invention provides a method for identifying a polymer having suitable bactericidal activity. In this method, a hydrophilizing first comonomer may be polymerized to a second comonomer and a bactericidal polymeric composition is formed. The bactericidal polymeric composition may be applied to a medium to form a first treated medium and the medium may be separately treated with the second comonomer used in the first treated medium. The first treated medium and the second treated medium may be separately contacted with a plurality of bacteria. Whether the first treated medium is more bactericidal than the second treated medium may be determined.

In a further example, a first polymeric composition and a second polymeric composition differing by molecular weight with regard to one or more corresponding comonomers may be separately applied to a medium and tested to identify a polymeric composition having improved bactericidal activity.

Alternatively, a first polymeric composition and a second polymeric composition differing by molar ratio of their corresponding comonomers may be varied and may be separately applied to a medium and tested to identify a polymeric composition having improved bactericidal activity.

In the above disclosed methods, a given polymeric composition may be rendered bactericidal by quaternization after polymerizing the hydrophilizing first comonomer to the second comonomer. Accordingly, the quaternized polymeric composition would be deemed suitable for use in a bactericidal composition if a medium containing or treated with the quaternized polymeric composition is more hydrophilic and/or bactericidal than the same medium containing or treated with the quaternized second comonomer alone.

Bactericidal activity may be evaluated using any suitable testing methodology used in the art, including, but not limited to, luminescence, optical density, or microscopic evaluation of bacterial growth or viability of coated and/or stained microscopic slides, plates or cultures.

The following examples illustrate features in accordance with the present invention, and are provided solely by way of illustration. They are not intended to limit the scope of the appended claims or their equivalents.

EXAMPLES

1. Radical Polymerization and Quaternization. Copolymers possessing suitable bactericidal properties and a suitable hydrophilicity/biocompatibility profile were obtained using a quaternized polymeric composition synthesized from 4-vinylpyridine and a biocompatible, hydrophilic comonomer, such as hydroxyethylmethacrylate (HEMA) or poly(ethyleneglycol) methacrylate.

Copolymers were synthesized by radical copolymerization with AIBN as initiator. The reactants were stirred at 70° C. for 48 hours under flowing $N_2$ to prevent oxidation. As the monomer contents were varied, the AIBN proportion was held constant to a mass ratio VP+PEGMA:AIBN equal to 22:1. To investigate the effects of hydrophilization, seven different compositions of VP with PEGMA300, PEGMA1100 and HEMA were synthesized, containing a molar percentage of VP of 10, 25, 50, 75, 90, 95 and 99.

Copolymers were quaternized with a 3-fold excess of hexyl bromide (HB) in a mixture of chloroform and methanol by reflux for 48 hr. They were precipitated in hexane, recovered and dried under vacuum. A schematic of the radical polymerization and quaternization process can be seen in FIG. 1.

Synthesis of P(VP-co-HEMA), P(VP-co-PEGMA300) and P(VP-co-PEGMA1100) was followed with FTIR and NMR. Spectroscopy showed that the synthesis was successful and that the quaternization went to near completion and that the resultant products were relatively pure after work-up.

VP, HEMA and PEGMA were purchased from Sigma Aldrich Co. (Milwaukee, USA). To avoid polymerization through heat or light, these monomers were inhibited with hydroquinone (HQ), 4-Methoxyphenol (MEHQ), and 2,6-di-tert-butyl-4-methylphenol (BHT) respectively. The HQ and MEHQ inhibitors were removed by means of trap to trap while BHT was purified from PEGMA by column chromatography on silica gel (70-270 mesh) stationary phase.

2. Contact Angle and Bactericidal Testing. To evaluate wettability or hydrophilicity, contact angle tests were conducted by dip coating microscope slides in solutions with copolymer dissolved in chloroform and methanol. Contact angle measurements were obtained on a Ramé-Hart Advanced Goniometer.

Bactericidal tests were performed with a small quantity of the bacteria *Escherichia coli* O157:H7 in which the lux gene was added for luminescence, which provides a measure of metabolic growth or activity. A sample was taken from a culture and placed in contact with the coated slides, by means of a pipette. The intensity of the bioluminescence was recorded as a function of time for two hours with a photomultiplier tube. Reduced bioluminescence correlates with enhanced bactericidal activity.

Figure 2:
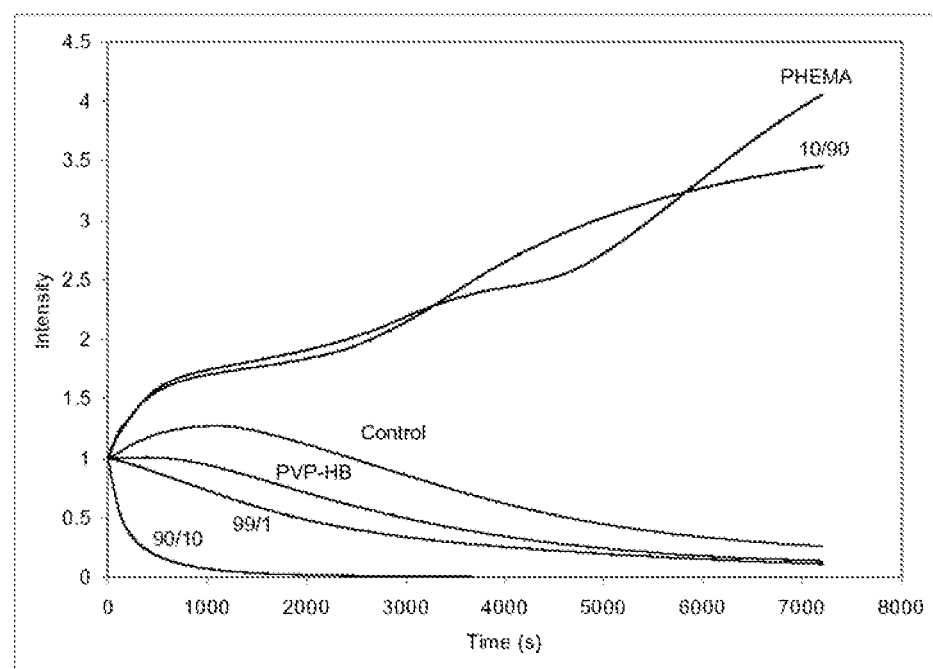
FIG. 2 is graph of bactericidal results for surface testing of P(VP-co-HEMA)-HB.

3. Bactericidal activity of P(VP-co-HEMA). The results of the bactericidal tests on quaternized copolymers of VP and HEMA are shown in FIG. 2. An initial increase of intensity is observed in the control, due to the fast growth of the bacteria, called blooming. After approximately 19 minutes, the intensity starts decreasing as the bacteria start to die. PVP-HB, known to kill bacteria, prevents blooming, as reflected by the fact that the intensity never increases by more than 1 percent. The intensity starts decreasing after only 7 minutes. Since this is much earlier than the control, the death of the bacteria can be attributed to the properties of the polymer. An uninterrupted blooming is observed for a slide coated with PHEMA, and the number of bacteria has quadrupled after two hours, following a lag-log behavior. This indicates that PHEMA by itself is not bactericidal.

P(VP-co-HEMA)-HB 95/5 and P(VP-co-HEMA)-HB 90/10 exhibited enhanced bactericidal activity compared to PVP-HB alone. The luminescence recorded for P(VP-co-HEMA)-HB 99/1, is similar to, but slightly less than that observed for PVP-HB alone. Accordingly, this copolymer, having one molar percent HEMA, displays properties similar to PVP-HB alone. However, a slide coated with P(VP-co-HEMA)-HB 99/1 kills bacteria faster than one coated with PVP-HB.

Figure 3:
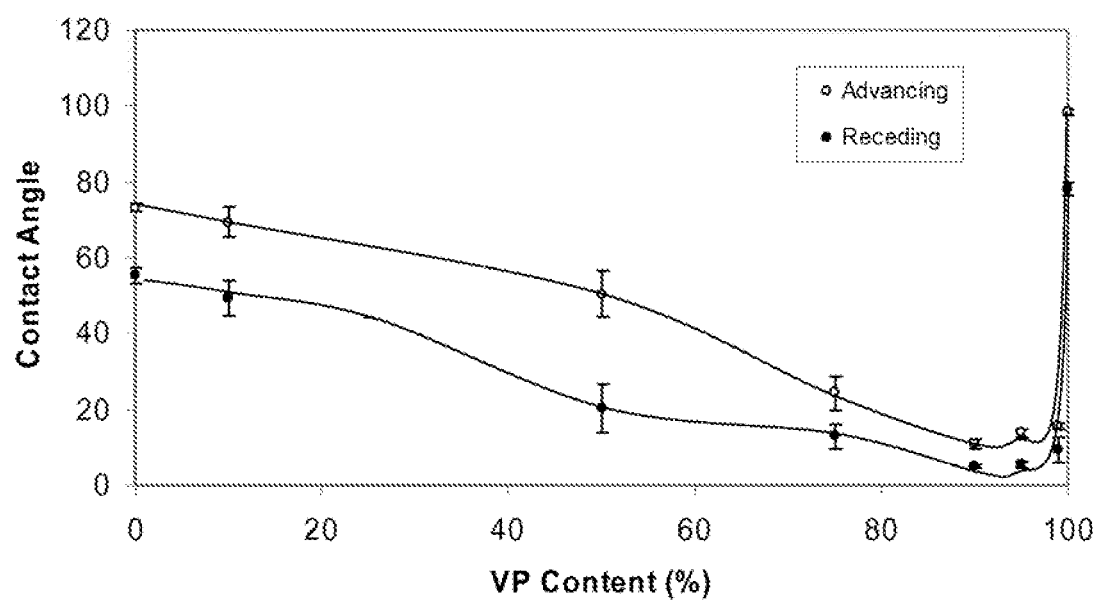
FIG. 3 is a graph of advancing and receding contact angles for P(VP-co-HEMA).

The wettability of dry, vitreous HEMA-based materials was studied by contact angle measurements. The results for both advancing and receding angles are given in FIG. 3. Contact angle measurements showed an increase in hydrophilicity provoked by the copolymerization. The surface energy was found to be minimal for P(VP-co-HEMA) at 90/10 and slightly higher for P(VP-co-HEMA)-HB 99/1. This corresponds to the bactericidal behavior of the polymers and suggests that the wettability plays a significant role in the polymer's effectiveness. Being a hydrogel monomer, HEMA hydrophilizes the copolymer.

Although not wishing to be bound by theory, it is believed that coupling hydrophilization to bactericidal activity in the polymer facilitates enhances bacterial killing, in part because of the water-loving nature of bacteria: a hydrophilic growth medium is better able to support uptake and killing by a hydrophilized bactericidal polymer compared to an unhydrophilized bactericidal polymer. Moreover, it is believed that the bactericidal polymers are electrostatically attracted to the bacterial cell wall whereby lipophilic side chains insert into the bacterial cell membrane, disrupting it so that holes form therein.

In P(VP-co-HEMA)-HB 90/10, the wettability effect is particularly evident. This polymer exhibits a more optimal bactericidal activity, reflected in the fact that all bacteria were killed in 30 minutes. This further illustrates that that a slide coated with P(VP-co-HEMA)-HB 90/10 copolymer is significantly more bactericidal than pure PVP-HB.

Figure 4:
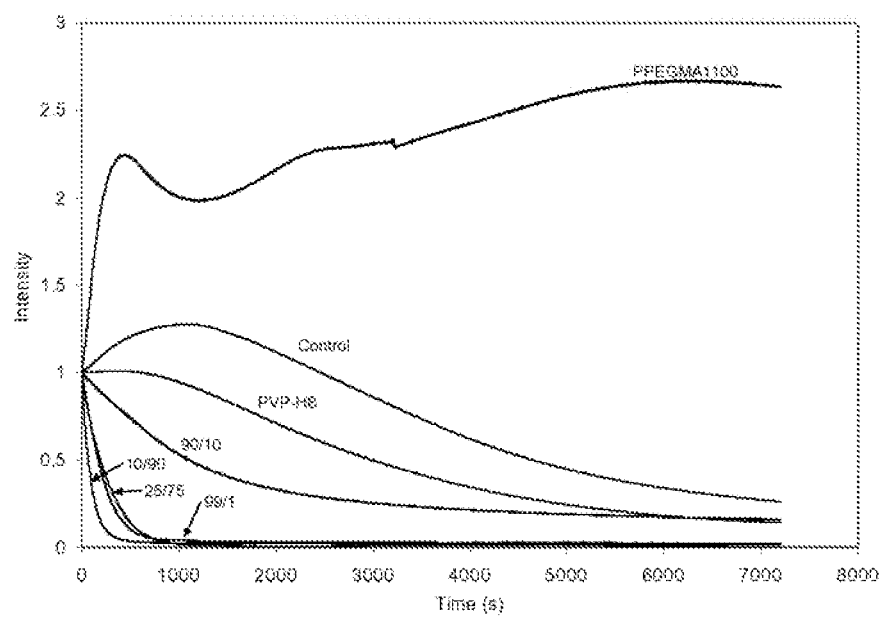
FIG. 4 is a graph of bactericidal results for testing of P(VP-co-PEGMA1100).

4. Bactericidal activity of P(VP-co-PEGMA). The bacterial growth behavior for copolymers with PEGMA1100 can be seen in FIG. 4. Comonomer ratios of 90/10, 25/75, and 10/90 exhibited enhanced bactericidal activity compared to PVP-HB alone. Extremely high bactericidal activity was seen with ratios of 99/1, presumably due to the large fraction of VP and improved wettability from PEGMA1100. Copolymers with ratios ranging from 95/5 to 50/50 displayed bacterial results similar to PVP-HB.

P(VP-co-PEGMA1100)-HB 25/75 and 10/90 displayed a surprisingly high antibacterial activity. Although counterintuitive, this fact can have several explanations. The molecular weight of P(VP-co-PEGMA1100)-HB 10/90 is much higher than other copolymer formulations of this system. This could increase bactericidal activity, because the copolymer possesses more alkyl tails to traverse the bacterial membranes. The enhanced water wettability of the polymer may enable the polymer to better dissolve in and/or surround the bacteria in an aqueous medium, so as to facilitate more efficient bacterial killing.

PPEGMA300 (graph not shown) alone does not kill bacteria and actually improves growth due to its biocompatibility and hydrophilicity. The improved biocompatibility and hydrophilicity is carried over into the P(VP-co-PEGMA300) copolymers with ratios from 0/100 to 50/50 thereby improving bacterial growth. However, for ratios greater 50/50, bactericidal activity was observed. The optimum balance between spreading and VP content was found to be 75/25, in which half the bacteria were killed in the first 15 minutes. Overall, the bactericidal behavior of the PEGMA300 based polymers were reduced compared to PEGMA1100 based polymers.

PEGMA1100 has a significantly larger PEG size than PEGMA300. A smaller fraction of PEGMA1100 is thus necessary to hydrophilize P(VP-co-PEGMA1100). However, even for some similarly hydrophilized polymers, the PEGMA1100 materials exhibit superior bactericidal activity, possibly due to the enhanced protein resistance imparted by longer PEG chains in the polymers.

The enhanced bactericidal activity exhibited by the HEMA and PEGMA copolymers appears to result from enhanced wettability in aqueous solutions, allowing the polymer to better surround and/or gain access to the bacteria, so as to enhance bacterial killing.

Figure 5:
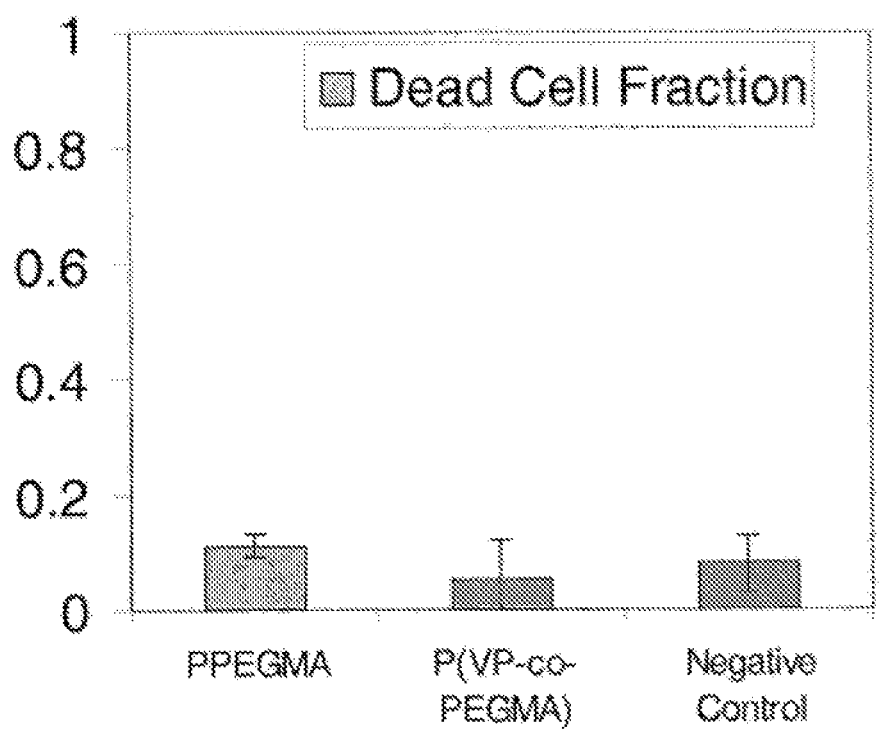
FIG. 5 is a bar chart plotting the fraction of dead epithelial cells as a function of added bactericidal polymer or polymer control.

5. Cytotoxity of P(VP-co-PEGMA). A viability/cytotoxicity assay may be used to evaluate biocompatibility of the bactericidal polymers for mammalian cells. In particular, FIG. 5 shows that an exemplary bactericidal PEGMA1100 copolymer is non-toxic to mammalian cells. Corneal epithelial cells were seeded onto polystyrene culture plates in phosphobuffered saline solution (PBS; pH 7.2) at a density of 3,500 cells/cm$^2$ for 24 hrs at 37° C. The cells were co-incubated for 4 hrs. with quaternized P(VP-co-PEGMA1100) copolymer or PPEGMA control polymer in PBS at a concentration of 2.5 mg/ml, along with a PBS negative control media.

Live cells were distinguished from dead cells using a fluorescence-based LIVE/DEAD viability/cytotoxicity assay system (Molecular Probes, Invitrogen Detection Technologies). The assay system includes two probes, calcein AM, a fluorogenic esterase substrate producing a green fluorescent product in live cells having intracellular esterase activity, and ethidium homodimer-1, a high-affinity, red fluorescent dye only able to pass through and stain the compromised membranes of dead cells. FIG. 5 plots the fraction of dead epithelial cells as a function of added bactericidal polymer or polymer control. As shown in FIG.

5, treatment of epithelial cells with the bactericidal P(VP-co-PEGMA) polymer did not exhibit a statistically significant level of epithelial cell killing over that of the PEGMA polymer or PBS negative controls.

It is to be understood that the above-described polymers and methods for their use are merely representative embodiments illustrating the principles of this invention and that other variations in the polymers or methods, may be devised by those skilled in the art without departing from the spirit and scope of this invention. The foregoing detailed description and accompanying drawings have been provided solely by way of explanation and illustration, and are not intended to limit the scope of the appended claims. Many variations in the presently preferred embodiments illustrated herein will be apparent to one of ordinary skill in the art, and remain within the scope of the appended claims and their equivalents.

What is claimed is:

1. A method of reducing a number of bacteria comprising
   a. contacting the bacteria and a bactericidal copolymer, and
   b. reducing growth of the bacteria with the bactericidal copolymer,
   c. wherein the bactericidal copolymer is a copolymer comprising
      i. a 4-vinyl pyridine, wherein the 4 vinyl pyridine is quaternized with an alkyl group; and
      ii. a hydrophilic comonomer comprising a PEG ester having an acrylate or a methacrylate group.

2. The method of claim 1, wherein the hydrophilic comonomer has the methacrylate group.

3. The method of claim 2, wherein the hydrophilic comonomer has a molar molecular weight of at least about 300.

4. The method of claim 3, wherein the hydrophilic comonomer has a molar molecular weight of less than about 2000.

5. The method of claim 4, wherein the hydrophilic comonomer has a molar molecular weight of about 1100.

6. The method of claim 2, wherein the bactericidal copolymer contains less than or equal to about 10 mole percent of the hydrophilic comonomer.

7. The method of claim 2, wherein the bactericidal copolymer contains less than or equal to about 95 mole percent of said 4-vinyl pyridine.

8. The method of claim 7, wherein the bactericidal copolymer contains less than or equal to about 75 mole percent of said 4-vinyl pyridine.

9. The method of claim 7, wherein the bactericidal copolymer contains less than or equal to about 50 mole percent of said 4-vinyl pyridine.

10. The method of claim 7, wherein the bactericidal copolymer contains less than or equal to about 25 mole percent of said 4-vinyl pyridine.

11. The method of claim 7, wherein said alkyl group is hexyl.

12. The method of claim 1, wherein said alkyl group is hexyl.

13. The method of claim 3, wherein the bactericidal copolymer consists essentially of said 4-vinyl pyridine quaternized with the alkyl group and the hydrophilic comonomer.

* * * * *